United States Patent [19]

Fenichel et al.

[11] 4,041,155
[45] Aug. 9, 1977

[54] LONG ACTING SOMATOSTATIN COMPOSITION

[75] Inventors: Richard L. Fenichel, Wyncote; Howard J. Levin, Norristown, both of Pa.

[73] Assignee: American Home Products Corporation, New York, N.Y.

[21] Appl. No.: 518,650

[22] Filed: Oct. 29, 1974

[51] Int. Cl.² ............... A61K 37/00; C07C 103/52
[52] U.S. Cl. ........................... 424/177; 260/112.5 S
[58] Field of Search ............... 424/177; 260/112.5 R

[56] References Cited

U.S. PATENT DOCUMENTS

| | | | |
|---|---|---|---|
| 2,975,099 | 3/1961 | Goyan et al. | 424/177 |
| 3,527,864 | 9/1970 | MacMillan et al. | 424/177 |
| 3,631,018 | 12/1971 | Shanbrom et al. | 424/177 |
| 3,652,530 | 3/1972 | Johnson et al. | 424/177 |
| 3,763,135 | 10/1973 | Shanbrom et al. | 424/177 |
| 3,845,204 | 10/1974 | Grant | 424/177 |

OTHER PUBLICATIONS

Gerich et al.: New Eng. J. Med., 291, 544–547 (1974).
Rivier: J. Am. Chem. Soc., 96, 2986–2992 (1974).
Sollmann, "Manual of Pharmacology," 8th ed., W. B. Saunders Co., Phila., 1957, pp. 128–130.
Brazeau et al.: Science, 179, 77–79 (1973).

*Primary Examiner*—Delbert R. Phillips
*Attorney, Agent, or Firm*—David E. Frankhouser

[57] ABSTRACT

An aqueous vehicle containing about 80% polyethylene glycol 400 or polyethylene glycol 300 imparts long-acting growth hormone release inhibiting activity to somatostatin or linear somatostatin.

3 Claims, No Drawings

LONG ACTING SOMATOSTATIN COMPOSITION

This invention relates to growth hormone-lowering compositions containing somatostatin or linear somatostatin. Said compositions have an improved duration of activity as compared to compositions heretofore employed.

Somatostatin is the cyclic disulfide tetradecapeptide of the formula:

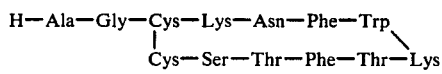

Linear somatostatin is the reduced tetradecapeptide of the formula:

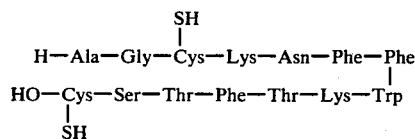

The cyclic form (I) differs from the linear form (II) in that a bridging bond is formed between the two sulfhydryls of two cysteinyl amino acid residues.

Somatostatin (I) can be isolated from hypothalamic extracts or it can be prepared by the oxidation of linear somatostatin prepared by total synthesis. The synthetic preparation of somatostatin and linear is described by Rivier et al., C. R. Acad. Sci. (Paris), 276, 2727 (1973) and Sarantakis et al., Biochemical and Biophysical Research Communications, 54, 234 (1973). Synthetic linear somatostatin and synthetic cyclic somatostatin both have the same biological activity as somatostatin obtained from natural sources.

Somatostatin is the "Somatotropin-release inhibiting factor" (SRIF) which is secreted by the hypothalamus and which regulates the secretion of growth hormone (GH) (also known as somatotropin) by the pituitary. See Brazeau et al., Science, 179, 77 (1973); Burgus et al., Proc. National Acad. Sci. (USA), 70, 684 (1973); and Ling et al., Biochemical and Biophysical Research Communications, 50, 127 (1973).

The GH-inhibiting activity of somatostatin and linear somatostatin has been demostrated in vitro and in vivo in laboraanimals and in humans. For example, Brazeau et al., Endocrinology, 94, 184 (1974) have shown that linear somatostatin given by the subcutaneous route lowers the circulating levels of GH in gentled rats and prevents the elevation of plasma GH concentration induced in rats by sodium pentobarbital. The duration of activity is short, the half-life being estimated as less than ten minutes.

The efficacy of synthetic somatostatin in the inhibition of chronic GH hyperseretion in patients with acromegaly has been reported by Yen et al., New England Journal of Medicine, 290, 935 (1974). The results suggest that the inhibitory action of somatostatin on GH secretion is nearly complete and that the biologic action is brief. In addition, somatostatin induces a concomitant fall in circulating levels of insulin, glucose, and prolactin and an increase in free fatty acids. No effects on levels of thyrotropin, follicle-stimulating hormone or luteinizing hormone were observed. It has also been reported by Mortimer et al., Lancet, 1974, 697 (April 20), that SRIF impairs the release of glucagon, insulin, and GH during oral glucose tolerance and intravenous arginine tests in healthy patients and in patients with arcromegaly, diabetes mellitus, or hypopituitarism. Other studies demonstrating the inhibition of GH release in humans by somatostatin are reported in the references cited in the above-described publications by Yen et al. and Mortimer et al. The effects of somatostatin and linear somatostatin on GH screation, insulin, and glucagon suggest that the compounds may be therapeutically useful in the treatment of diabetes.

It is well known that the duration of biological activity of exogenous somatostatin or linear somatostatin is short, and a need exists for a long acting preparation. Heretofore, long acting effects were obtained with preparations containing linear somatostatin adsorbed on protamine zinc.

In accordance with the present invention, there is provided a long-acting growth hormone release-inhibiting composition suitable for subcutaneous or intramuscular injection comprising:

a. Somatostatin or linear somatostatin, and
b. an aqueous vehicle containing about 80% polyethylene glycol 400 or polythylene glycol 300.

In practicing the invention, the somatostatin or linear somatostatin is dissolved in a measured volume of water and sufficient polyethylene glycol 400 or polyethylene glycol 300 is added to the solution to afford the desired concentration. For example, formulations containing either 500 μg/ml or 400 μg/ml of somatostatin are prepared by dissolving 500 μg or 400 μg of omatostatin in 0.2 ml of water and then adding thereto, with stirring, 0.8 ml of polyethylene glycol 400. The formulations so prepared can be pre-mixed long prior to use or can be prepared immmediately before use. If desired, pharmaceutically acceptable preservatives and/or suspending agents can be included in the formulation in small effective amounts.

Although the exact mechanism is not known, it is believed that the somatostatin or linear somatostatin is finely dispersed in the vehicle with the result that absorption is retarded after injection.

It will be appreciated that the concentration of somatostatin or linear somatostatin in the vehicle is governed by the solubility of the active ingredients, the volume of the formulation to be administered, and the dosage desired. Moreover, the concentration of somatostatin or linear somatostatin must not be so great that the volume of vehicle is too small to retard the rate of absorption. In general, a concentration of from about 100 μg/ml to about 800 μg/ml of somatostatin or linear somatostatin will provide satisfactory results. A concentration of from about 300 μg/ml to about 600 μg/ml is preferred.

The prolongation of GH-release inhibition by somatostatin or linear somatostatin in the vehicle as hereinabove defined has been demonstrated in tests in rats by the following method:

A single subcutaneous (SC) injection of somatostatin or linear somatostatin in the vehicle is administered to a group of rats at a dose of 400 μg/kg (about 80 μg per rat). Blood is obtained for GH determination from separate groups of rats 2 and 4 hours after the injection. Control groups of rats for each time period are given vehicle alone. Sodium pentobarbital, which induces GH secretion, is administered by the intraperitoneal route (50mg/kg.) either 20 minutes or one hour before blood is obtained for the GH determination. Non-fasted rats are use since sodium pentobarbital induces higher GH levels in these animals. The GH levels in the blood samples are assayed by the radioimmune method described by Siler et al., *J. Clin. Endocrinol. Metab.*, 37, 632 (1973).

With a formulation containing 400 μg of somatostatin per ml. in a vehicle containing 80% polyethylene glycol 400 and 20% water, the following results are obtained.

|  | Plasma GH (μg/ml) | |
|---|---|---|
|  | 2 Hours | 4 Hours |
| Control | 114 ± 14 (32)* | 150 ± 21 (32)* |
| Somatostatin | 58 ± 8 (33)* | 81 ± 12 (34)* |

*Number of animals. Data is pooled from four identical experiments.

With a formulation identical to that described above except that polyethylene glycol 300 is used in place of polyethylene glycol 400, the following results are obtained.

|  | Plasma GH (μg/ml) | |
|---|---|---|
|  | 2 Hours | 4 Hours |
| Control | (a) 299 ± 89 (7)* | 221 ± 71 (7)* |
|  | (b) 625 ± 161 (7)* | 137 ± 51 (7)* |
| Somatostatin | (a) 88 ± 23 (6)* | 120 ± 34 (7)* |
|  | (b) 557 ± 156 (8)* | 197 ± 74 (6)* |

*Number of animals. Data obtained from two experiments shown as (a) and (b).

The results with the polyethylene glycol 400 preparation show that a significant lowering of plasma GH concentration occurs at 2 hours and at 4 hours after injection. With the polyethylene glycol 300 preparation, a significant lowering of plasma GH concentration occurs at 2 hours. With conventional vehicles for somatostatin (i.e. physiological or buffered saline), the in vivo activity of somatostatin, even with high doses, is lost after 15 minutes to 30 minutes.

The effective dose of somatostatin or linear somatostatin is that which will maintain the serum GH concentration within normal or desired limits. Serum GH concentrations can be determined by radioimmunoassay see Siler et al., *J. Clin.. Endocrinol. Metab.*, 37, 632 (1973). In general, a single subcutaneous or intramuscular injection of from about 75 to about 600 μg of somatostatin or linear somatostatin per animal will provide long-acting suppression of GH release.

As used herein "polyethylene glycol 400" means the polymer of ethylene oxide and water represented by the formula $H(OCH_2CH_2)_nOH$, in which the average value of n lies between 8.2 and 9.1. Said polymer is described in the *U. S. Pharmacopeia*, Revision XVIII (1970), page 514. "Polyethylene glycol 300" means the polymer of ethylene oxide and water represented by the formula $HOCH_2(CH_2OCH_2)_nCH_2OH$ where the average value of $n$ lies between 5 and 5.75. It has an average molecular weight of from 285 to 315. Said polymer is described in the *National Formulary*, XIII, p. 562 (1970).

What is claimed is:

1. A long-acting growth hormone release-inhibiting composition suitable for subcutaneous or intramuscular injection comprising:
   a. Somatostatin or linear somatostatin, and
   b. an aqueous vehicle containing about 80% polyethylene glycol 400.

2. A composition as defined in claim 1 comprising somatostatin and an aqueous vehicle containing about 80% polyethylene glycol 400.

3. A composition as defined in claim 1 comprising linear somatostatin and an aqueous vehicle containing about 80% polyethylene glycol 400.

* * * * *